United States Patent
LaPeyronnie et al.

(10) Patent No.: US 7,739,918 B1
(45) Date of Patent: Jun. 22, 2010

(54) ADHESION TESTING DEVICE

(75) Inventors: Glenn M. LaPeyronnie, Gretna, LA (US); Charles M. Huff, Slidel, LA (US)

(73) Assignee: Lockheed Martin Corporation, Bethesda, LA (US)

( * ) Notice: Subject to any disclaimer, the term of this patent is extended or adjusted under 35 U.S.C. 154(b) by 330 days.

(21) Appl. No.: 12/035,259

(22) Filed: Feb. 21, 2008

(51) Int. Cl.
   *G01N 3/08* (2006.01)
(52) U.S. Cl. ....................................... 73/827
(58) Field of Classification Search ............. 73/150 A, 73/150 R, 827
   See application file for complete search history.

(56) References Cited

U.S. PATENT DOCUMENTS

| | | | |
|---|---|---|---|
| 4,114,434 A * | 9/1978 | Hauser | 73/150 R |
| 4,548,083 A * | 10/1985 | Schuerer et al. | 73/827 |
| 5,795,990 A * | 8/1998 | Gitis et al. | 73/9 |
| 6,584,858 B1 * | 7/2003 | Miyazawa et al. | 73/827 |

OTHER PUBLICATIONS

Erichsen, "Adhesion and Tensile Test Instrument" Adhesion Master 525 MC.
DeFelsko, "PosiTest Pull-Off Adhesion Tester" DeFelsko Corporation 2005.
Instron, "In-Spec 2200 Portable Testers" Instron Corporation 2003.

* cited by examiner

*Primary Examiner*—Lisa M Caputo
*Assistant Examiner*—Octavia Davis
(74) *Attorney, Agent, or Firm*—Jones, Walker, Waechter, Poitevent, Carrere & Denegre

(57) ABSTRACT

The present invention provides a testing apparatus and method for testing the adhesion of a coating to a surface. The invention also includes an improved testing button or dolly for use with the testing apparatus and a self aligning button hook or dolly interface on the testing apparatus. According to preferred forms, the apparatus and method of the present invention are simple, portable, battery operated rugged, and inexpensive to manufacture and use, are readily adaptable to a wide variety of uses, and provide effective and accurate testing results. The device includes a linear actuator driven by an electric motor coupled to the actuator through a gearbox and a rotatable shaft. The electronics for the device are contained in the head section of the device. At the contact end of the device, is positioned a self aligning button hook, attached below the load cell located on the actuator shaft.

7 Claims, 4 Drawing Sheets

Thermal Protection Bond Tension Tester

Figure 1:
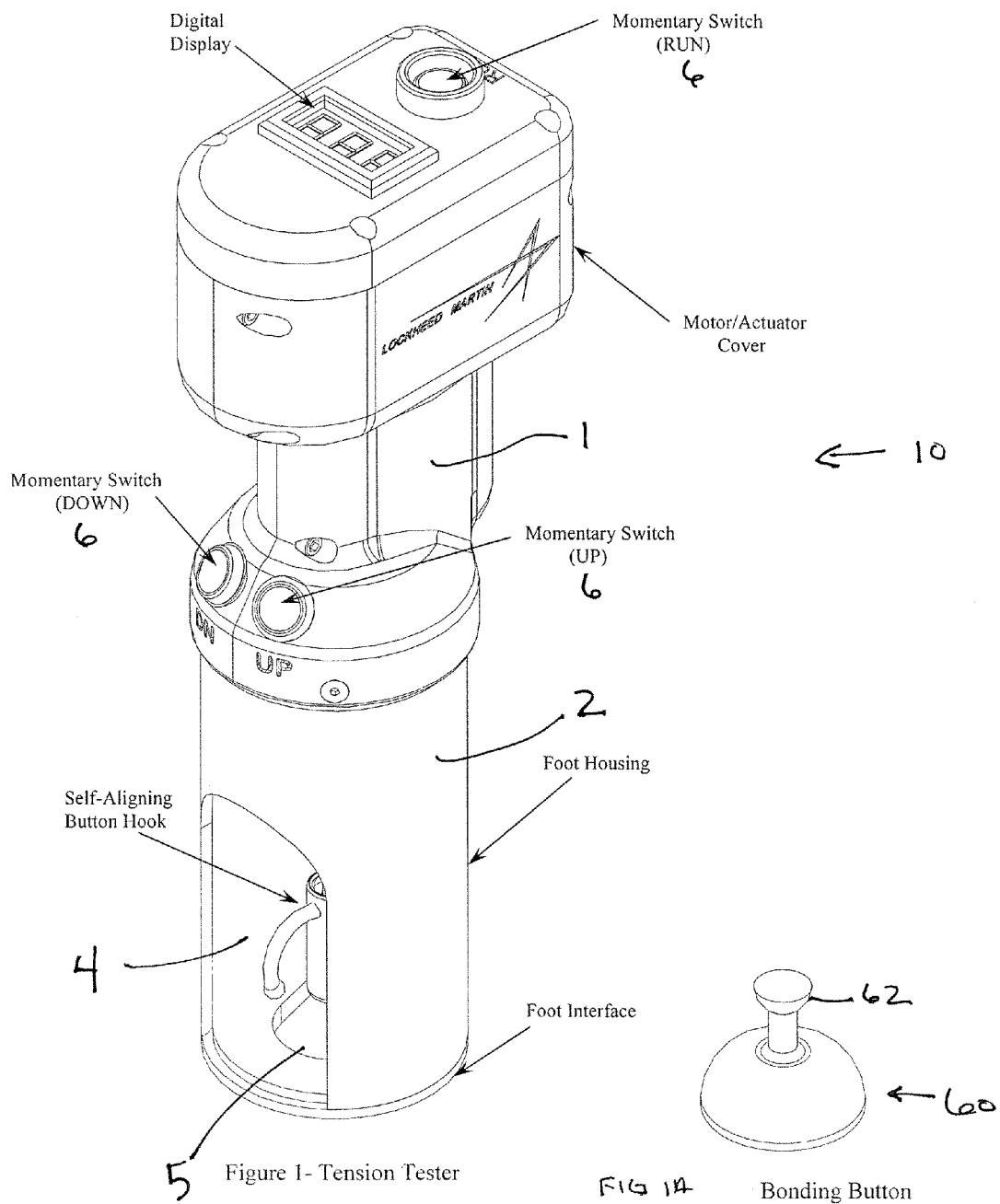

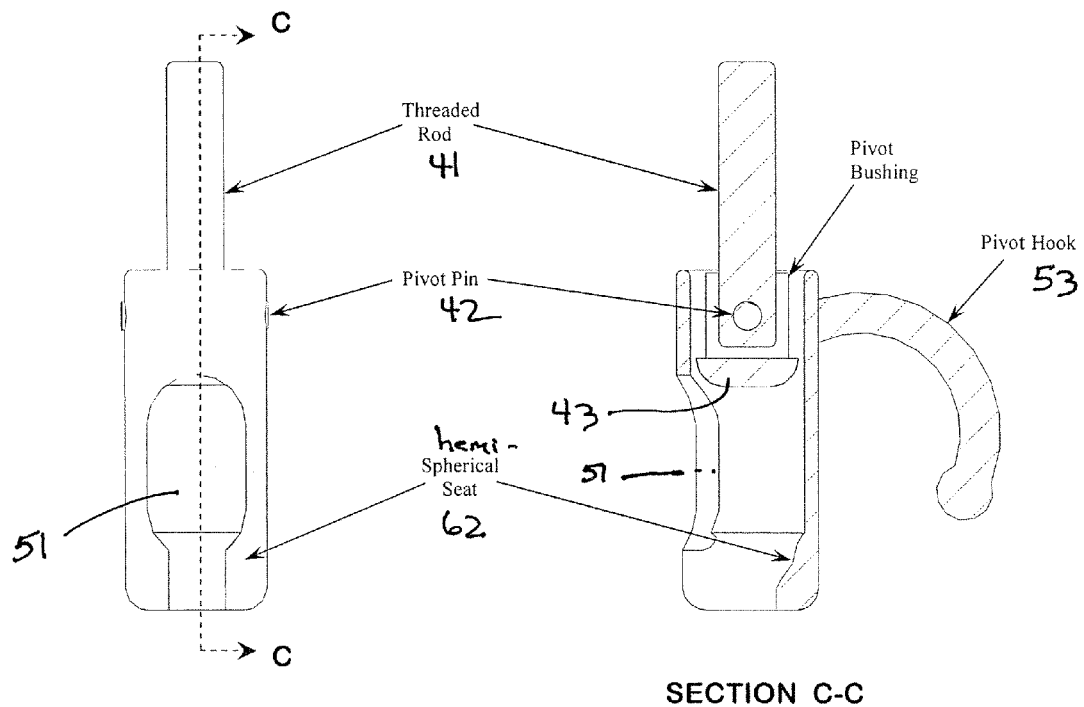
FIG 3B                    FIG 3A
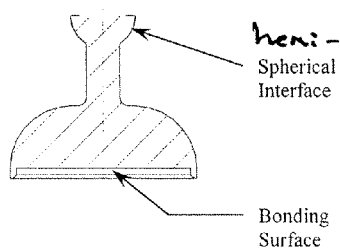
Bonding Button Section
FIG 3C

ADHESION TESTING DEVICE

FUNDING

The U.S. Government has certain rights to this application and invention pursuant to the terms of Contract No. 453631 82500 32200 awarded by the National Aeronautics and Space Administration (NASA).

FIELD OF THE INVENTION

The present invention relates generally to materials testing, and more particularly to a device and method for measuring the adhesion strength of a coating to a substrate.

DESCRIPTION OF RELATED ART

A variety of coatings are commonly applied to surfaces of substrates to enhance or otherwise alter characteristics of the substrate. For example, coatings such as corrosion barriers, moisture barriers, vapor barriers, thermal barriers such as sprayed form insulation and sheet materials are often applied to substrates formed of materials such as metals, cementitious materials, wood, or plastics. The durability and longevity of a coating for its particular purpose is highly dependent on the strength of the adhesion to the substrate over which it is applied. The ability to measure the adhesion strength of coatings is a useful quality control criterion that is sometimes used for acceptance or rejection of coatings application work, and/or to compare the relative qualities of different coating materials.

Currently, there are several commercial devices for testing the coating adhesion. For instance, Erichsen GmbH in Germany markets the Adhesion Master 525 MC, DeFelsko of Ogdensburg, N.Y., markets the Positract adhesion tester. Many of the coating adhesion test devices that are currently available have been found to be unwieldy in use and unduly complex and expensive, especially for routine testing in the field. Many current testing devices use pneumatic actuators to apply the pulling or tensile force, but it has been found that it is difficult to consistently control the rate of pull for pneumatic controlled devices, and can create excessive shock to the load cell in the devices. Thus, it can be seen that needs exist for improved methods and devices for testing the adhesion of a coating to a substrate. It is to the provision of methods and devices meeting these and other needs that the present invention is primarily directed.

SUMMARY OF THE INVENTION

The present invention provides a testing apparatus and method for testing the adhesion of a coating to a surface. The invention also includes an improved testing button or dolly for use with the testing apparatus and a self aligning button hook or dolly interface on the testing apparatus. According to preferred forms, the apparatus and method of the present invention are simple, portable, battery operated rugged, and inexpensive to manufacture and use, are readily adaptable to a wide variety of uses, and provide effective and accurate testing results. The device includes a linear actuator driven by an electric motor coupled to the actuator through a gearbox and a rotatable shaft. The electronics for the device are contained in the head section of the device. At the contact end of the device, is positioned a self aligning button hook, attached below the load cell located on the actuator shaft.

Still another aspect of the present invention provides a method of testing the adhesion of a coating to a substrate. The method preferably includes coring through the coating to the substrate, and attaching a test dolly or button to the core (generally with high strength epoxy). The method preferably further includes coupling a testing device to the test dolly, and applying an increasing tensile force to the dolly until the coating releases from the substrate. The method preferably further includes storing the applied tensile force in the device for later download. These and other features and advantages of the present invention are described herein with reference to the drawing figures, or will be readily apparent to those skilled in the art having been provided with the teaching herein. The tool is particularly useful for testing the adhesion of the insulating layer of the NASA space shuttle external tank.

BRIEF DESCRIPTION OF THE DRAWING FIGURES

Figure 2:
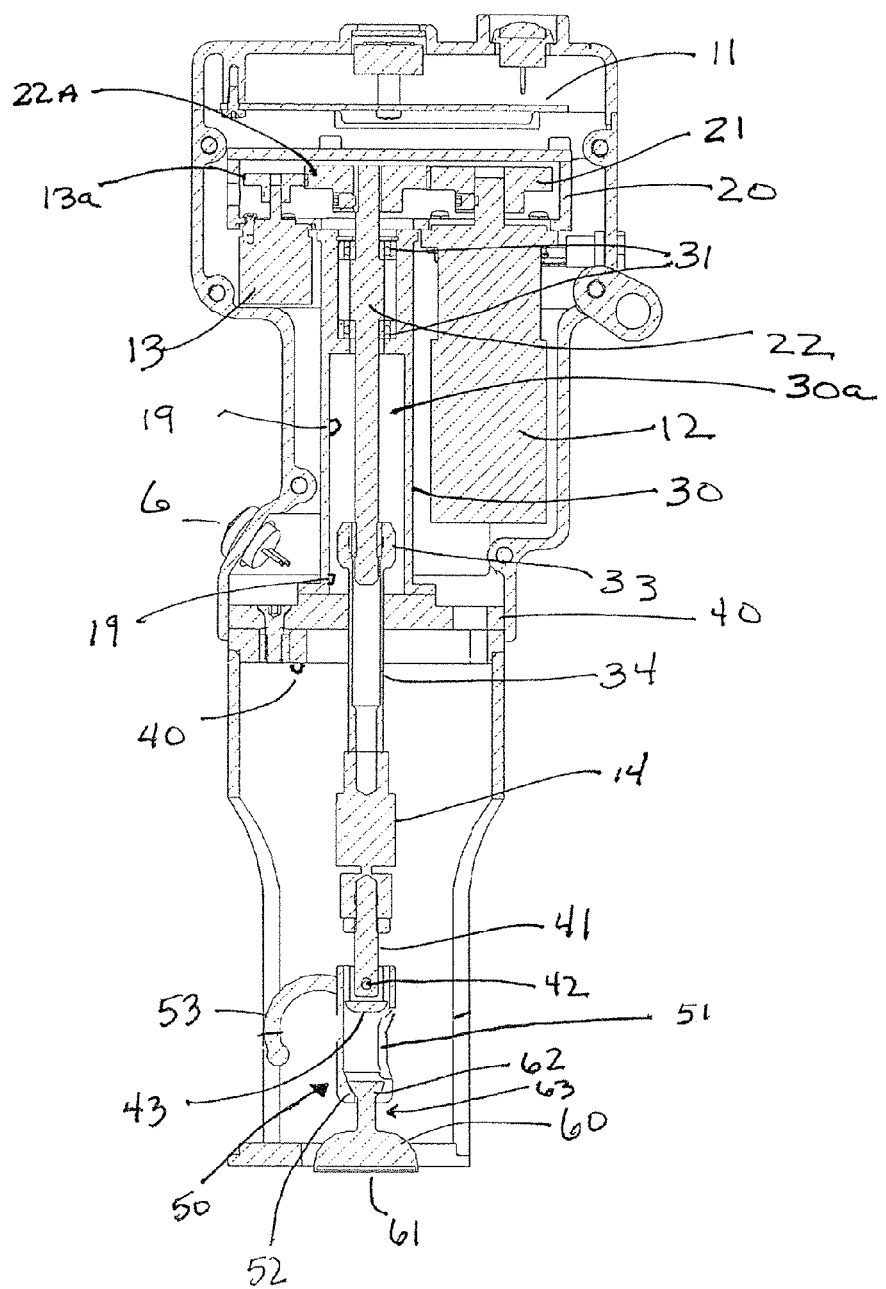
Figure 4:
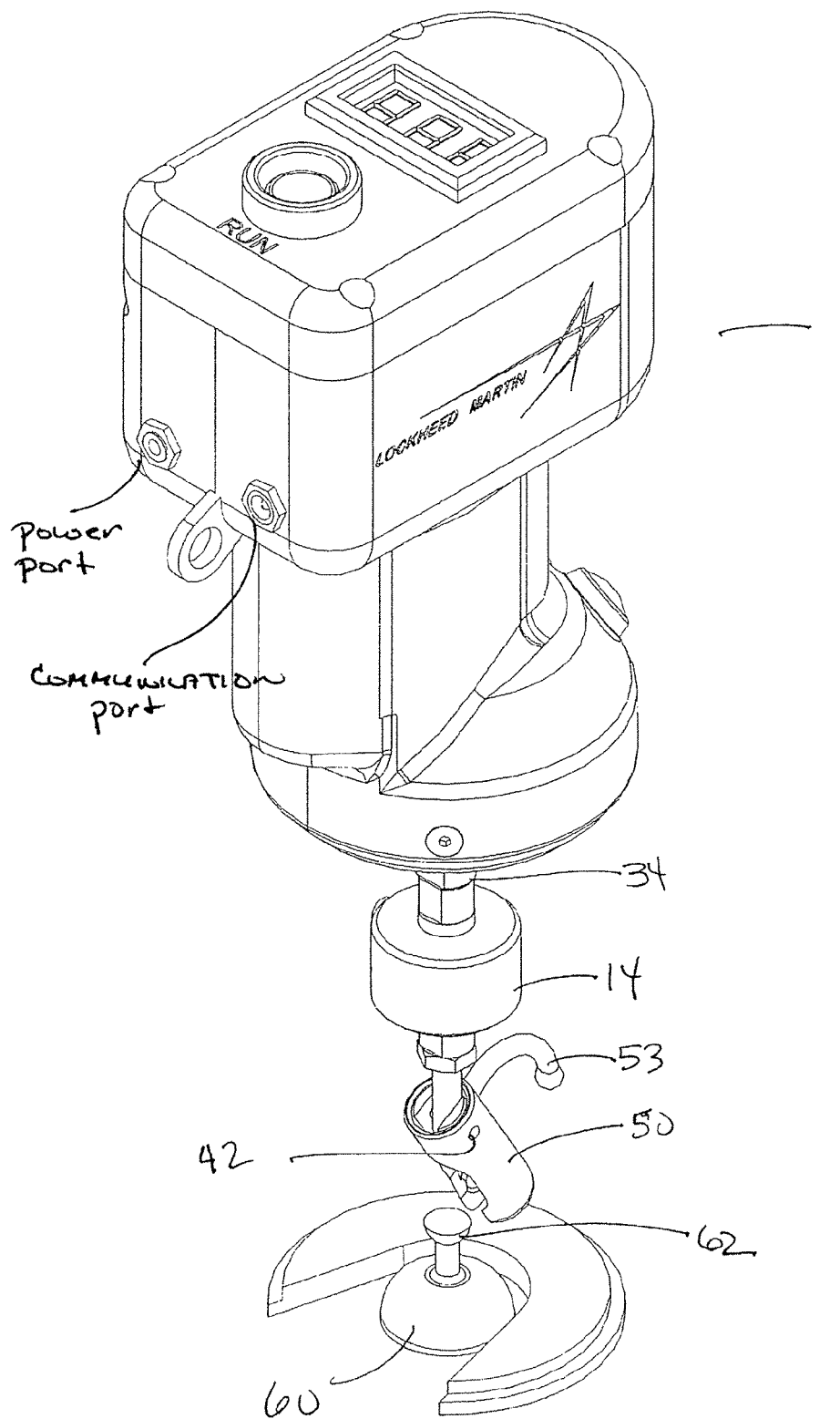

FIG. 1 shows a perspective view of a testing device.
FIG. 2 shows a cross sectional view of the testing device of FIG. 1.
FIG. 3A shows detail perspective view of the button engagement section
FIG. 3B is a cross section through of the button engagement section of FIG. 3A.
FIG. 4 is a prospective view of one embodiment of a button.

DETAILED DESCRIPTION

Referring now to the drawing figures, wherein like reference numerals represent like parts throughout, the testing device and method, and the test dolly of the present invention will now be described with reference to preferred embodiments. It is to be understood that the embodiments described and depicted herein are intended as examples to provide an understanding of the invention, but that the invention is not limited to the specific embodiments described.

A first preferred embodiment of the testing device 10 of the present invention is shown in FIGS. 1-4. The device 10 preferably comprises a hollow body 3 having a head section 1 and a tail section 2. Positioned on top of the head section is a visual indicator 15, and a control buttons 6. The tail section 2 is either open at bottom 5, or has an open slot in a bottom panel. Tail section 2 also has a side slot 4 to allow access to the button engagement section 43 later described. The components disposed within the substantially hollow body 3 of the device 10 are more readily seen in FIG. 2.

Located at the top interior of the body 3 is a circuit board having the relevant electronics located therein, such as memory, PLC or a CPU if desired, and controlling circuitry interconnecting and controlling the various electronic/electrical devices associated with the device, such as the electric motor 12, motor controls 6, load cell 14, encoder 13, limit switches 19 and LEDs 40. Located below the circuit board 11 is a gear box 20. Gear box 20 mechanically couples the drive shaft gear 22a and rotatable encoder head or gear 13a to the electrical motor through motor gear 21, allowing each to rotate in response to the motor 12. The motor is reversible. The gear ratio between the encoder head 13a and drive shaft 22a is predetermined, and with this relationship known, the reading for the encoder may be translated with appropriate electronics or software to a relative position of the actuator (such as height from a reference or start position). As shown a rotary optical encoder is used, but a linear encoder may also be employed with suitable modifications. Drive shaft 22 is positioned in actuator housing 30 and supported in a center bore 30a in the housing 30 by bearings 31.

Collar 33 is located at the upper end of actuator 34, and is coupled to drive shaft 22 by interior threads that ride on external facing threads on drive shaft 22. Actuator 34 extends downwardly from collar, and extends though center bore of plate 40 and is keyed or splined through this center bore to prevent actuator 34 from rotating. Hence rotation of drive shaft 22 is translated in to a linear up and down movement of actuator 34. Located in center bore 30a are limit switches 19 that interact with collar 33. Collar 33 protrudes sufficiently about drive shaft 22 to interact with limit switches 19. Head of device 1 is coupled to tail of device 2 though screws, bolts or other attachment means though plate 40.

Attached to lower end of actuator is load cell 14, which is in electrical communication with circuit board 11 components. Coupled to load cell 14 is button hook shaft 41. At the lower end of button hook shaft 41 is positioned a pivot pin 42 which couples with a pivot bushing 43. Pivot pin 42 engages a button engagement section 50, thereby allowing button engagement section 50 to pivot about axis of actuator.

Button engagement section is shown in further detail in FIGS. 3A-3B. As shown, button engagement section has a side slot 51, and a semi-hemispherical seat 52 positioned in the interior of the button engagement section. Button engagement section includes a hook 53 to allow an operator to grasp the hook 53 and position the orientation of the button engagement section as desired.

Shown in FIGS. 1A and 3C is a button 60. Button has a flat bottom facing surface 61 and a centered upstanding stem 62 which terminates in a semi-hemispherical interface section 62. Interface section is sized to rest on semi-hemispherical seat 52 located in the interior of the button engagement section 50. The button 60 is inserted into a seating position by sliding the interface section 62 of button 60 into the side slot 51 of button engagement section and positioning interface section 62 above the seat 52, and then positioning the button until the semi-hemispherical surfaces and seat face one another to allow the interface section 62 to rest on seat 52 (see FIG. 4). The design of the button/interface ensures the button is centered with respect to the axis of the actuator shaft 34. In this fashion, the tensile forces applied to the engaged button will be normal to the button bottom face, and applied in a uniformly motion which prevents rocking of the button or non-normal forces, which produces inaccurate readings.

In alternate embodiments, the arrangement of the cooperating surface features can be accomplished using comprise other forms of releasable engagement means such as, for example, inter engaging threads, ball-and-socket connectors, hooked or offset features, magnetic connections, connector links, inter engaging projections and recesses, and/or other types of cooperating surface features. Various manufactures for some of the components include Omron Electronics of Schaumburg, Ill. for switches; Grayhill of LaGrange, Ill. for encoders (for instance Series 63Q optical encoder); Globe Motors of Dayton Ohio for electrical motor (such as the CMM & CLL Gearmotors, model E-2030) (DC)); Honeywell International of Morristown N.J. for load sells (such as model 31 and 34 miniature load cells); Bescor of Farmingdale, N.Y. for battery packs, such as the NMH90 model).

Operation of the Device

In operation, the button can be first engaged with the device 10, and then attached to the coating, such as with epoxy. Prior to engagement with the dolly or button, the coating is cored down to the substrate to create a surface detached from the remainder of the coating. The cored area is generally circular shaped, usually created with a hole saw type attachment for a drill, thereby creating a cylindrical bore surface. The core is slightly smaller than the bottom surface of the dolly or button for the button shown in FIG. 1A. A particular embodiment uses a button with an outside bottom diameter of 1.125 inches, and the contact area of the button being 1.0 inch diameter. Hence the cored area should be no larger than 1.0 inche. The button may also be attached to the coating, and after the epoxy sets, the device is attached to the button 60. This versatility is allowed through the pivoting feature of the button engagement section. If the actuator needs to be lowered to allow the connection, the motor can be actuated to lower the actuator using the up/down jog buttons on the housing. Once the button is attached to the coating and coupled to the device, the motor can be actuated to raise or lower the device into a "zero" position or a "start" position, with the bottom of the base of the device even with the button bottom. Upon starting the run, counters are initiated for a new record or the test run. From the starting position, the run button is hit, starting a sequence of events that comprises a test run: (a) with motor actuation, the gear box transfers the rotation action to the drive shaft; (b) as the drive shaft turns, the actuator moves linearly up, by action of the mating threads; (c) raising the actuator results in a tensile force applied to the coating through the button; (c) the actuator will continue to rise until the coating pulls lose from the substrate, or the upper limit switch is reached and activated by contact with the collar, turning the device off. During the run, information is recorded in memory on the device, such as load cell reading and encoder reading (either direct or translated by onboard software or firmware in to a position above relative start position or other reference point), time or elapsed time, etc.

Current operational settings of the device are as follows: sample rate of 25 millisecond, record length of 255 samples, where each sample includes: sample number, load; distance from start position. Other information can be recorded as desired. The actuator rate is adjustable between 2-15 inches/minute, with 3 inches/min preferred for testing the foam coating on the exterior fuel tank.

While a test is underway, the device is recording the outputs from the load cell and the output of the encoder (the recorded encoder outputs may be modified through a counter circuit, to allow recordation of the counts for the encoder, or alternatively, the counts may be modified to represent the linear displacement of the actuator—all such are considered "encoder outputs" as each can be calculated from the actual outputs of the encoder, the current embodiment stores the actuator distance traveled from the starting position). Hence, for a given test, the device provides a recorded time sequence of values of load cell and encoder outputs, and each time sequence may have a time stamp for time from "start" of sequence (a sample stamp is equivalent with a known sample rate) or elapsed time if a summation circuit is employed). Additionally, the device outputs a selected reading to the visible display. A preferred reading would be the peak applied load, hence recorded loads are compared against a prior peak, and if the recorded load exceeds the peak, it replaces the peak and is displayed.

Enough memory should be provided to allow sufficient fine sampling of the data set, say for a 2.5 second run sampling every 0.025 second. When the button releases, the load cell output will drop sharply. This sharp drop may be configured in the system software as a halt. Alternatively the operator may disengage the motor, or the top limit switch may be reached prior to button release, thereby halting the process (this could occur, for instance with very elastic coatings).

As described, the device records the linear movement of the actuator (related to the strain on the coating) and the load cell output, related to the stress on the coating. The recorded data may be downloaded to a PC though a data output port for later analysis. Sufficient memory is kept onboard to allow 5-10 separate tests to be stored before memory is exhausted. Additional memory can be added for additional test sets.

Additional features can be added to the device 10, such downward pointing LED's to illuminate the test area. The device may include self test features, such as battery condition, load cell overload, limit switch activation, and a calibration sequence. The device may also include a calibration lockout, to disable the device after a designated number of runs unless a calibration sequence is run.

The device as shown and described is only one embodiment of the invention and the inventions should not be so limited.

What is claimed is:

1. A device for testing the adhesion of a coating to a substrate, said device comprising:
   a body having a head portion and a tail portion; said body having an internal cavity, said device having an electrical motor disposed therein operationally connected to a movable linear actuator, an encoder positioned in said device and operationally connected to said linear actuator for determining the relative position of said linear actuator, said device further having a button hook engagement section for releasingly engaging a button, said button hook engagement section pivoting about an axis through said linear actuator, said tail portion terminating in a contact area open to said internal cavity, a load cell operationally connected to said linear actuator, and a visual display mounted on said device.

2. The device of claim 1, wherein said button hook engagement section includes a hollow shaft having a semi-hemispherical seat and a slot positioned in said shaft providing access to said seat.

3. A method of testing the adhesion of a coating to a cylindrical bore surface, comprising:
   (a) gluing a button to a cylindrical bore surface, said button terminating in a semi-hemispherical interface section
   (b) attaching said button to the providing adhesion testing device comprising a body having a head portion and a tail portion; said body having an internal cavity, said device having al motor disposed therein operationally connected to a movable linear actuator, an encoder positioned in said device and operationally connected to said linear actuator for determining the relative position of said linear actuator, said device further having a button hook engagement section for releasingly engaging a button, said button hook engagement section pivoting about an axis through said linear actuator, said tail portion terminating in a contact area open to said internal cavity said button hook engagement section includes a hollow shaft having a semi-hemispherical seat and a slot positioned in said shaft providing access to said seat, and a load cell operationally connected to said linear actuator, and a visual display mounted on said device; and attaching said button to said adhesion testing device of claim 2 by pivoting said button hook engagement section adjacent said button interface section, slidingly inserting said button into said hollow shaft and seating said button interface section onto said seat of said button hook engagement section;
   (c) actuating said motor whereby said linear actuator is moved upwardly at a controlled rate by applying a normal tensile force to said coating through said button; and
   (d) monitoring said tensile force to render an indication of the force used to destructively pull the coating attached to said button away from the coated surface.

4. The device of claim 1, wherein said tail portion includes a sidewall forming a cavity, a portion of said actuator disposed in said cavity, said sidewall having a slot in said sidewall providing access to said cavity.

5. The device of claim 1 further having an onboard memory.

6. The device of claim 5 further having an interface port wherein data stored in said memory is downloadable to an external processing device.

7. The device in claim 1 wherein said encoder is an optical encoder.

* * * * *